(12) United States Patent
Kropf et al.

(10) Patent No.: US 7,615,038 B2
(45) Date of Patent: Nov. 10, 2009

(54) DISPOSABLE DIAPER WITH SEALABLE ENCLOSURE AND METHOD FOR SEALING AND DISPOSING OF THE SAME

(76) Inventors: Keith E. Kropf, 1434 S. 15$^{th}$ Ave. West, Newton, IA (US) 50208; Andrew E. Kropf, 1434 S. 15$^{th}$ Ave. West, Newton, IA (US) 50208

( * ) Notice: Subject to any disclaimer, the term of this patent is extended or adjusted under 35 U.S.C. 154(b) by 1250 days.

(21) Appl. No.: 10/777,251

(22) Filed: Feb. 12, 2004

(65) Prior Publication Data

US 2005/0182375 A1    Aug. 18, 2005

(51) Int. Cl.
*A61F 13/15* (2006.01)
*A61F 13/20* (2006.01)
*A61B 17/06* (2006.01)
*A61B 19/02* (2006.01)
*A61L 15/00* (2006.01)

(52) U.S. Cl. .............. 604/385.01; 604/385.06; 604/385.13; 604/385.19; 206/438; 206/439; 206/440

(58) Field of Classification Search ........... 604/385.01, 604/385.06, 385.13; 206/438–440
See application file for complete search history.

(56) References Cited

U.S. PATENT DOCUMENTS

| | | | | | |
|---|---|---|---|---|---|
| 3,369,545 | A | * | 2/1968 | Wanberg | ............... 604/385.13 |
| 3,731,689 | A | * | 5/1973 | Schaar | ............... 604/370 |
| 3,865,110 | A | * | 2/1975 | Traverse | ............... 604/365 |
| 3,877,432 | A | * | 4/1975 | Gellert | ............... 604/385.13 |
| 3,927,674 | A | * | 12/1975 | Schaar | ............... 604/385.13 |
| 4,034,760 | A | | 7/1977 | Amiraskis | |
| 4,085,753 | A | | 4/1978 | Gellert | |
| 4,493,713 | A | * | 1/1985 | Izzo | ............... 604/385.13 |
| 4,551,145 | A | * | 11/1985 | Ryan | ............... 604/389 |
| 4,790,840 | A | | 12/1988 | Cortina | |
| 4,808,175 | A | | 2/1989 | Hansen | |
| 4,964,859 | A | * | 10/1990 | Feldman | ............... 604/385.06 |
| 5,071,414 | A | * | 12/1991 | Elliott | ............... 604/385.13 |
| 5,141,505 | A | * | 8/1992 | Barrett | ............... 604/385.13 |
| 5,304,158 | A | * | 4/1994 | Webb | ............... 604/385.13 |
| D366,315 | S | | 1/1996 | Oranday | |
| D386,582 | S | | 11/1997 | Levine | |
| 6,063,067 | A | | 5/2000 | Takizawa et al. | |
| 6,210,386 | B1 | * | 4/2001 | Inoue | ............... 604/385.13 |
| 6,454,748 | B1 | * | 9/2002 | Ives | ............... 604/385.06 |

* cited by examiner

*Primary Examiner*—Patricia M Bianco
*Assistant Examiner*—Susan Su

(57) ABSTRACT

A disposable diaper is provided comprising a diaper body having an outer surface. The disposable diaper includes a waterproof layer secured to an outer surface layer of the diaper body to form a pocket between the layer and the outer surface. The disposable diaper further comprises means for sealing the pocket to seal in waste and odor. A method for sealing and disposing of the diaper also is provided, comprising the steps of rolling the diaper inwardly toward the pocket, inverting the pocket to receive the diaper body, and sealing the pocket to enclose the diaper body.

5 Claims, 5 Drawing Sheets

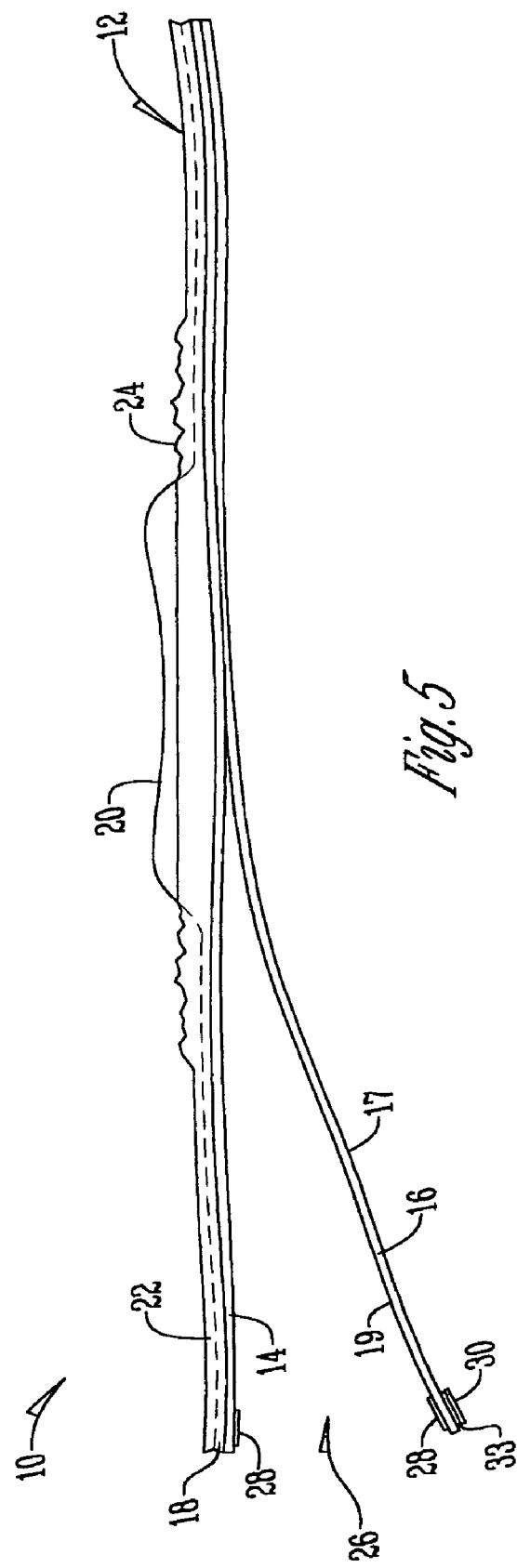

DISPOSABLE DIAPER WITH SEALABLE ENCLOSURE AND METHOD FOR SEALING AND DISPOSING OF THE SAME

BACKGROUND OF THE INVENTION

The present invention relates to a disposable diaper and, more specifically, a disposable diaper with a sealable enclosure for containing waste and sealing in odor. The present invention also relates to a method for sealing and disposing of the diaper.

Largely because of their convenience, disposable diapers have been transformed from something of a laboratory experiment fifty years ago to becoming a staple in millions of households worldwide. A majority of parents now use disposable diapers on their children, contending that disposable diapers not only provide greater convenience, but perform better and keep their babies dryer than traditional cloth diapers. Disposable diapers also have found large markets with the elderly and infirm, and even some pet owners use disposable diapers on their dogs.

Although there have been tremendous advances in disposable diaper technology, particularly in the past twenty years, the problem still remains of what to do with a soiled disposable diaper following use. While soiled diapers containing only urine may be tossed into a trash receptacle often times without incident, the same is not true with soiled diapers containing more. As any parent will attest, the odor emanating from a truly soiled disposable diaper creates quite a problem.

U.S. Pat. No. 6,170,240 to Jacoby et al. discloses a container in which soiled disposable diapers are deposited. By turning a knob on the top of the Jacoby et al. device, a soiled diaper is enveloped in plastic wrapping to seal in the odor and waste. Through using the Jacoby et al. device, a parent may dispose of soiled diapers in such a way that the odor is contained and does not proliferate throughout the house.

One disadvantage of conventional devices for the odor-free disposal of soiled diapers, such as that disclosed by Jacoby et al., is that they require the use of a special dispenser or trash receptacle that is costly and takes up valuable space in the baby's nursery. In addition, these conventional devices must be emptied. Typically, these devices hold upwards of twenty soiled diapers, all strung together in a chain of plastic wrapping. Emptying of these conventional devices therefore can become messy and inconvenient.

U.S. Pat. No. 4,085,753 to Gellert discloses a disposable diaper with an integral disposal bag. Specifically, the Gellert device includes a large backing separate from the diaper that forms a pocket wherein the pocket is inverted to encase the diaper. One disadvantage of the Gellert device is that the diaper is merely folded in half prior to disposal, leaving a parent with a bulky soiled diaper. A greater disadvantage of the Gellert device is that it does not seal in odors. Offensive odors are allowed to drift out of the disposal bag taught by Gellert and permeate throughout the house.

It is therefore a principal object of this invention to provide a method and device for disposing of soiled diapers that does not require the use of a separate dispenser or trash receptacle.

A further object of this invention is to provide a disposable diaper with a sealable enclosure that contains the waste and seals in offensive odors.

These and other objects will be apparent to those skilled in the art.

BRIEF SUMMARY OF THE INVENTION

The present invention is directed toward a disposable diaper comprising a diaper body having an outer surface. The disposable diaper includes a waterproof layer secured to an outer surface layer of the diaper body to form a pocket between the layer and the outer surface. The disposable diaper further comprises means for sealing the pocket to seal in waste and odor.

The present invention also is directed toward a method for sealing and disposing of the diaper comprising the steps of rolling the diaper inwardly toward the pocket, inverting the pocket to receive the diaper body, and sealing the pocket to enclose the diaper body.

BRIEF DESCRIPTION OF THE DRAWINGS

FIG. 5 is a sectional view of the disposable diaper of the present invention showing an alternative embodiment.

DESCRIPTION OF THE INVENTION

Figure 2:
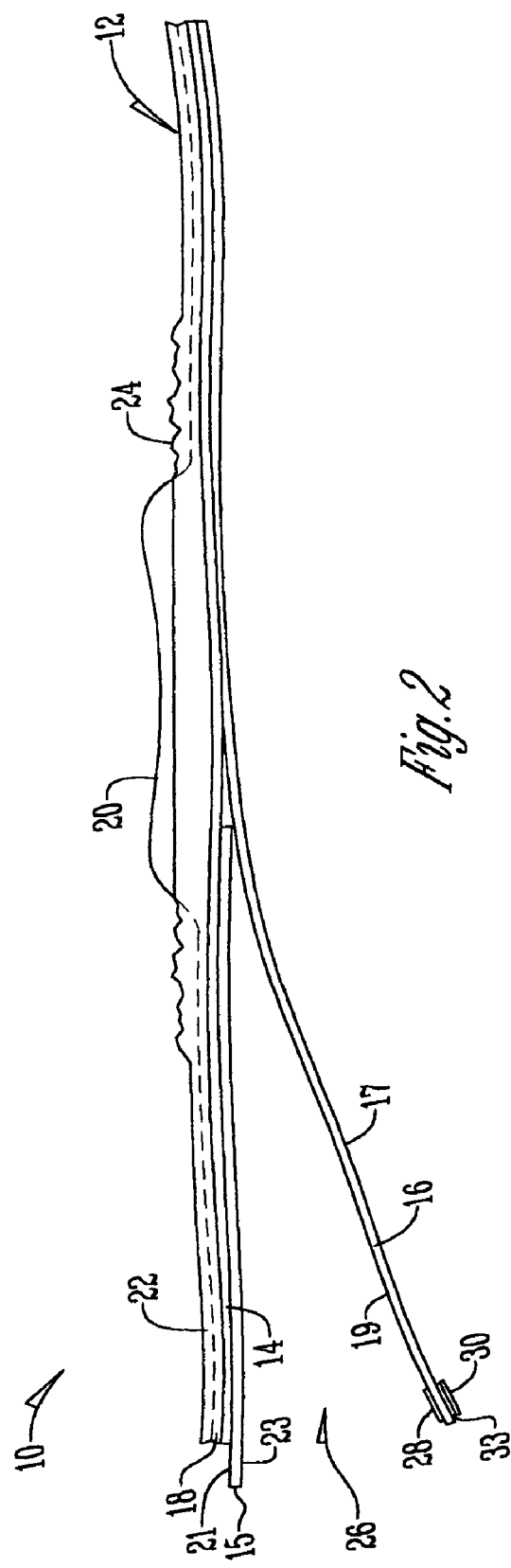
FIG. 2 is a sectional view of the side of the disposable diaper illustrating the layers of the present invention.

With reference to the drawings, a disposable diaper 10 is shown with a body 12. As best shown in FIG. 2, the body 12 is comprised of several layers. Outer layer 14, which typically serves as a backing for conventional diapers, forms the basis upon which layers 15 and 16 are attached. Outer layer 14 typically is composed of a cloth-like material and is leak resistant. Layers 15 and 16 are preferably composed of a plastic or other waterproof material to form a leak-proof barrier. In a preferred embodiment, the body 12 of diaper 10 also includes a middle layer 18, which secures an absorbent pad 20. Diaper body 12 further includes a top layer 22, which secures elastic leggings 24.

Layer 15 is secured to outer layer 14 of the diaper body in any conventional manner or alternatively can extend around the diaper body 12 and is secured to the top layer 22. While diaper 15 can extend the length of the diaper body 12, extending only a portion of the length is preferred to save material. The securing end of layer 15 extends beyond the diaper body 12 to facilitate a better water and odor tight seal.

Figure 1:
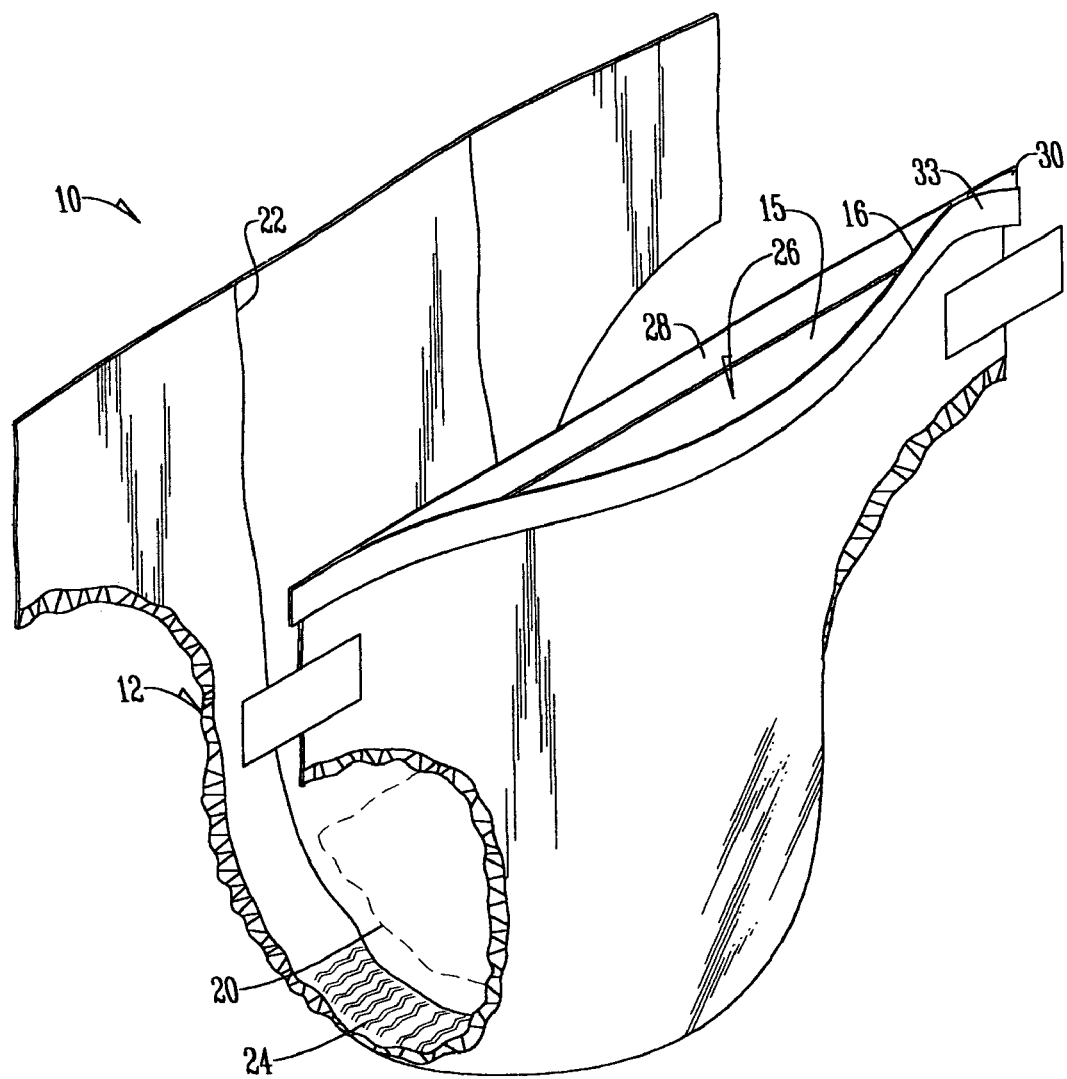
FIG. 1 is a perspective view of the disposable diaper of the present invention.

Layer 16 secures to layer 15 of diaper 10 to form a pocket 26, as best shown in FIGS. 1 and 2. Pocket 26 is positioned such that its opening is to the rear of the child when the diaper 10 is being worn.

Main seal 30 is attached to the exterior or first surface 17 of layer 16, as best shown in FIG. 2. After diaper 10 has been prepared for disposal, main seal 30 allows diaper 10 to be secured such that waste and odor are sealed within diaper 10, as described below. In a preferred embodiment, main seal 30 is a tape strip or similar adhesive type seal. In addition, main seal 30 may include a protective facing 33 that is removed prior to sealing to expose and activate the tape strip.

As an optional feature, a seal 28 is attached to the interior or second surface 19 of layer 16, as best shown in FIG. 2. Seal 28 allows pocket 26 to be secured in a closed position, particularly when the diaper 10 is worn. In a preferred embodiment, seal 28 is a tape strip or similar adhesive type seal. Seal 28 is constructed such that pocket 26 may be opened once.

While the disposable diaper 10 is being worn, the pocket 26 is in the closed position, allowing the pocket 26 to be used for holding a wipe or moistened toilette. If desired following use, disposable diaper 10 is removed from the child. Pocket 26 is pulled to the open position, thereby breaking seal 28. Wipes stored within the pocket 26 may be removed and used for cleaning the child.

Figure 3A:
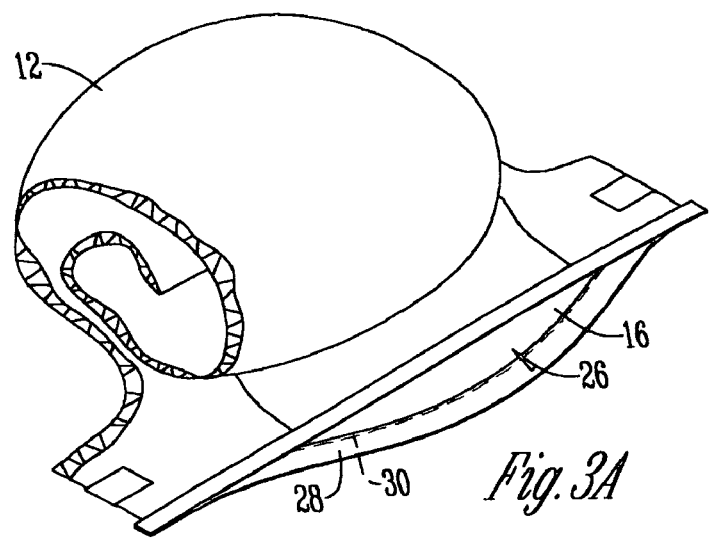
FIGS. 3A, 3B, and 3C are perspective views of the disposable diaper, illustrating the manner in which a soiled disposable diaper of the present invention may be sealed following use.
Figure 3B:
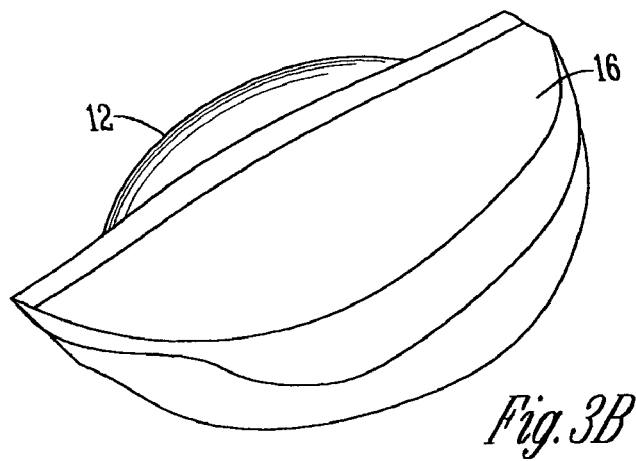
Figure 3C:
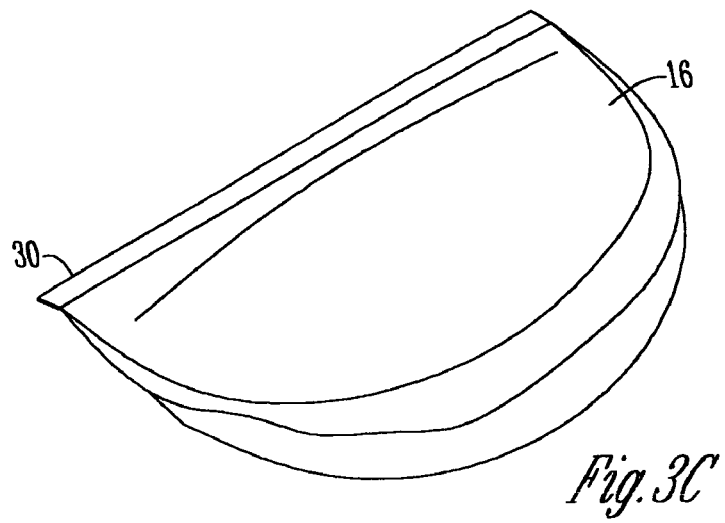

The disposable diaper 10 is then prepared for disposal. As shown in FIG. 3A, the soiled diaper 10 is rolled inwardly towards the pocket 26. By rolling the diaper 10 inwardly, waste is trapped within the diaper body 12. Pocket 26 is then inverted to receive the rolled up diaper 10, as shown in FIG. 3B. Pocket 26 completely encases the soiled, rolled up diaper 10, as shown in FIG. 3C. Upon inverting the pocket 26 about the diaper 10, the main seal 30 on the first surface 17 of layer 16 is engaged with a first surface 21 on layer 15 to seal in waste and odor. Specifically, the protective facing 33 of the seal 30 is removed to expose the adhesive tape strip, which is pressed firmly against the first surface 21 of layer 15 of the diaper body 12 to create an airtight seal. The sealed, rolled up diaper 10 then can be placed in any trash receptacle for disposal without the proliferation of offensive odor.

Figure 4:
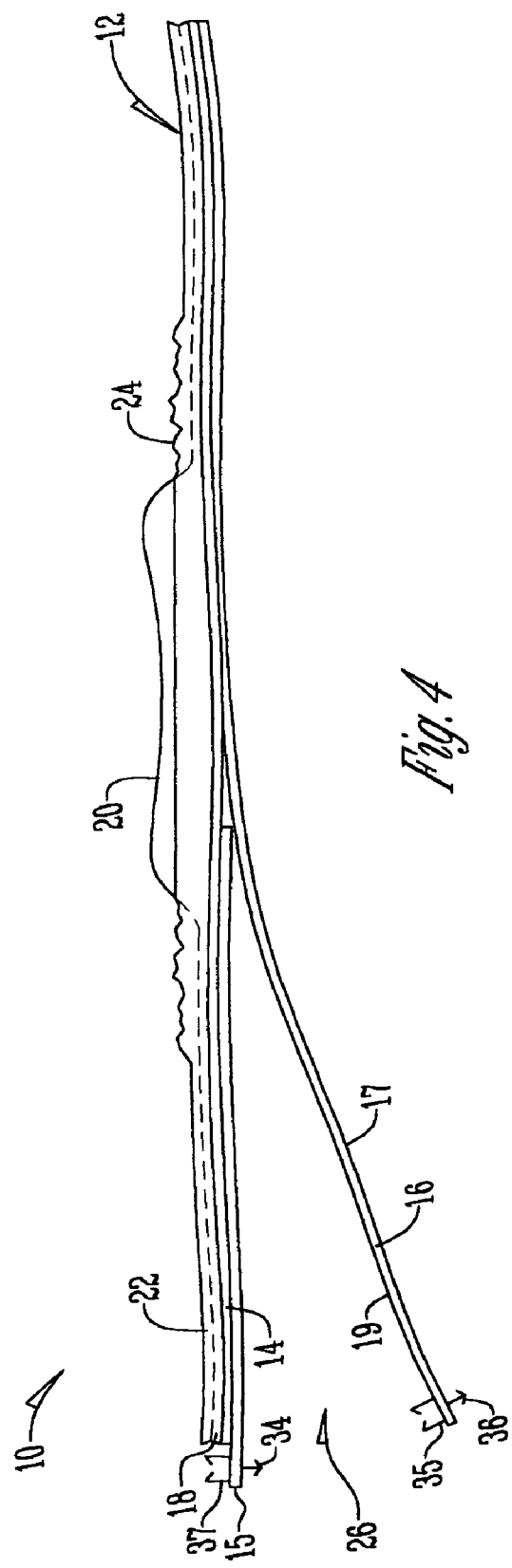
FIG. 4 is a sectional view of the disposable diaper of the present invention showing an alternative sealing means.

Alternatively, seals 28 and 30 may be airtight interlocking closures, such as "ziplock" type seals. As shown in FIG. 4, seal 30 is comprised of a male bead 34 mounted on the first surface 17 of layer 16 and a female slot 36 mounted on the first surface 21 of layer 15. Seal 28 is comprised of a male bead 38 mounted on a second surface 23 of layer 15 and a female slot 40 mounted on a second surface 19 of layer 16. Seals 28 and 30 may be modified "ziplock" seals such that the interlocking beads have barbed profiles that firmly lock together and resist separation as shown in FIG. 4. Such a modified "ziplock" type seal prevents seals 28 and 30 from easily opening after being manually pressed shut.

In yet another alternative embodiment, layer 16 is directly connected to the diaper body 12 to form a pocket 26 between outer layer 14 and layer 16. Main seal 30 is secured by engaging top layer 22 when pocket 26 has been inverted to receive the soiled diaper.

It is therefore seen that by the use of a sealable enclosure incorporated into the body of a disposable diaper, this invention permits the odor-free disposal of a soiled diaper without the use of a separate dispenser or trash receptacle.

What is claimed is:

1. A disposable diaper comprising:
    a diaper body having an outer surface;
    a first layer secured to the diaper body;
    a second layer having an interior surface secured to the diaper body to form a pocket between the first and second layer; and
    a means for sealing the pocket for containing waste and odor on an exterior surface of the second layer.

2. The disposable diaper of claim 1 wherein the first layer and the second layer are waterproof.

3. The disposable diaper of claim 1 wherein the sealing means is a tape strip attached to a first surface of the second layer.

4. The disposable diaper of claim 1 wherein the tape strip has a releasable protective facing.

5. The disposable diaper of claim 1 wherein the sealing means is an interlocking closure.

* * * * *